United States Patent
Socci et al.

(10) Patent No.: US 6,565,835 B1
(45) Date of Patent: May 20, 2003

(54) NAIL ENAMEL COMPOSITIONS CONTAINING ALUMINUM PLATELETS

(75) Inventors: Robert L. Socci, Cedar Grove, NJ (US); Anatoly Ismailer, Roslyn Heights, NY (US)

(73) Assignee: Kirker Enterprises, Inc., Patterson, NJ (US)

( * ) Notice: Subject to any disclaimer, the term of this patent is extended or adjusted under 35 U.S.C. 154(b) by 30 days.

(21) Appl. No.: 09/611,900

(22) Filed: Jul. 7, 2000

(51) Int. Cl.[7] ............ A61K 6/00; A61K 7/00; A61K 7/04
(52) U.S. Cl. ............................ 424/61; 424/401
(58) Field of Search ................... 424/61, 401

(56) References Cited

U.S. PATENT DOCUMENTS

| | | | | |
|---|---|---|---|---|
| 3,438,796 A | * | 4/1969 | Hanke | 106/291 |
| 4,116,628 A | * | 9/1978 | Hesse et al. | 427/154 |
| 4,192,691 A | * | 3/1980 | Armanini | 106/291 |
| 5,093,108 A | * | 3/1992 | Pappas et al. | 424/61 |
| 5,346,692 A | | 9/1994 | Wohlrab et al. | |
| 5,688,494 A | * | 11/1997 | Graves et al. | 424/61 |
| 5,977,217 A | * | 11/1999 | Socci et al. | 524/35 |
| 5,993,837 A | | 11/1999 | Calello et al. | |
| 6,139,822 A | * | 10/2000 | Socci et al. | 424/61 |

* cited by examiner

Primary Examiner—Thurman K. Page
Assistant Examiner—S. Howard
(74) Attorney, Agent, or Firm—Lerner, David, Littenberg, Krumholz & Mentlik, LLP

(57) ABSTRACT

Nail enamel compositions of the present invention for coating natural or synthetic human nails broadly include the ingredients of one or more film forming components, one or more solvents and aluminum particles in the form of platelets. The resulting composition will provide a nail enamel which forms a film upon drying having a mirrorlike appearance.

81 Claims, No Drawings

NAIL ENAMEL COMPOSITIONS CONTAINING ALUMINUM PLATELETS

FIELD OF THE INVENTION

The present invention relates in general to nail enamel compositions, and more particularly, to nail enamel compositions containing aluminum platelets for forming a film having a mirrorlike appearance over natural or synthetic human nails.

BACKGROUND OF THE INVENTION

Nail enamel compositions include a class of nail care products regularly used by women as part of their beauty care routine. These nail care products are available in a multitude of product formulations, from clears to a variety of colors. Typically, clear nail enamel compositions include a film forming polymer, a film forming resin, a plasticizer and one or more solvents. In the case of a color nail enamel composition, the product may also include a thixotropic compound, a suspending agent and one or more pigments, or in the alternative, an organic coloring polymer may be used. In addition to these components, a number of optional and proprietary components are often included such as UV light absorbers, moisturizers, stabilizers, fragrances and the like.

Nail enamel compositions have heretofore been formulated in an infinite number of colors. Often, the manufacturers would produce nail enamel compositions having the same popular colors as their competitors. This provided little distinction between nail enamel products of different manufacturers to the ultimate consumer. Nail enamel compositions having a more decorative appearance were produced by including small pieces of light reflecting, decorative material known as glitters within the composition.

Other attempts to enhance the decorative appearance of nail enamel compositions has been the use of metallic pigments. By way of example, there has been known the use of metallic pigments in the nature of aluminum platelets having a controlled particle size and uniform thickness. Aluminum platelets of the foregoing characteristics which have been incorporated into nail enamel compositions are available from Avery Dennison Corporation of Pasadena, Calif. which are sold under the mark Metalure® through Obron Atlanta Corp. of Hainesville, Ohio. The aluminum platelets are supplied in a dispersion or suspension as a slurry dispersed in various solvents compatible for formulation in vehicles for rotogravure and flexographic printing inks, and in base vehicles and clear coats for spray applications.

The nail enamel composition incorporating aluminum platelets contained nitrocellulose RS ½ sec. (M.W. –56,000) as the film forming component. The films when applied over natural or synthetic human nails had a generally dull silver appearance. Although the silver appearance provided a unique and decorative look to the nail enamel composition, the dull nature detracted from its aesthetic value. The metallic appearance was further deteriorated by the inclusion of suspending agents required to support the aluminum platelets in the nail enamel composition.

Despite these known nail enamel compositions having aluminum platelets, there has heretofore been unknown nail enamel compositions which when applied to natural or synthetic human nails will produce a film having a mirrorlike appearance.

SUMMARY OF THE INVENTION

The present invention discloses a nail enamel composition having a mirrorlike appearance. The nail enamel composition includes aluminum particles in the nature of platelets which, in accordance with one example, are sold under the mark Metalure®. The Metalure® dispersions or suspensions are commercially available in eight different vehicles systems as follows:

| Metalure® Product No. | Aluminum N.V.M. | Solvent (1% Acetone) | Viscosity (Avg.) | Wt/Gal. Lbs. |
|---|---|---|---|---|
| L-53520 | 10% | 89%-Toluene | 840 cps | 7.8 |
| L-54893 | 10% | 89%-Normal Propyl Acetate | 35 cps | 7.9 |
| L-54894 | 10% | 89%-Isopropyl Acetate | 160 cps | 7.75 |
| L-54949 | 10% | 89%-Isopropyl Alcohol | 540 cps | 6.61 |
| L-55350 | 10% | 89%-Ethyl Acetate | 20 cps | 8.1 |
| L-55700 | 10% | 89%-Ektasolve ® (Methyl Proposol Acetate) PM Acetate | 320 cps | 8.5 |
| L-56161 | 10% | 89%-Glycol Ether PM | 1000 cps | 8.23 |
| L-56716 | 10% | 89%-Normal Butyl Acetate (NBAC) | 600 cps | 8.13 |

The preferred dispersion or suspension of aluminum platelets are those dispersed in ethyl acetate, Metalure® Product No. L-55350. In addition to being dispersed in a solvent compatible in nail enamel compositions, it has a relatively low viscosity compared to the other available dispersions or suspensions. The low viscosity is preferred in view of the high molecular weight film forming components incorporated into the nail enamel composition of the present invention as to be described. However, it is to be understood that the other designated dispersions or suspensions of the aluminum platelets, and mixtures thereof, can also be incorporated into the nail enamel compositions of the present invention, including those from other sources. For example, aluminum platelets are also available from Silberline Manufacturing Co., Inc. of Tamaqua, Pa. under the mark STARDRITE 1100 EAC. The aluminum platelets are provided as a 10% dispersion in ethyl acetate. Aluminum platelets are also available from MD-Both Industries of Ashland, Mass. under the marks Metasheen NC Dispersion and Metasheen N1000 Dispersion. The aluminum platelets are provided as a 5% dispersion in a mixed organic solvent/nitrocellulose base.

As previously discussed, nail enamel compositions incorporating aluminum platelets have heretofore been known. These compositions were based upon incorporation of aluminum platelets in nitrocellulose RS½ sec. as the film forming component. The percent solids in the known composition was in the range of about 25–32% by weight. The known nail enamel composition although having an aluminum color appearance did not have a mirrorlike appearance, i.e., having a dull silver appearance.

In accordance with the present invention, it has been discovered that nail enamel compositions containing aluminum platelets can be formulated to have a mirrorlike appearance. To this end, it has been discovered that by incorporating one or more film forming components into the nail enamel composition having higher molecular weights, the resulting composition will produce a film having a mirrorlike appearance. The film forming component can be selected from a variety of polymers such as those well known for use in nail enamel compositions. As a result of the higher molecular weight film forming components, the solid content of the nail enamel composition is generally lower than heretofore known, for example, in the order of about 4 to about 20% by weight.

In accordance with one embodiment of the present invention there is described a nail enamel composition of non-toxic components for forming a film over natural or synthetic human nails, the composition comprising a film forming component, a solvent and aluminum platelets, the film having a haze value greater than 932 HU. Non-toxic components include those components which are suitable for use in nail enamel compositions. Toxic compounds which are not suitable for use in nail enamel compositions include those which have been banned under state or federal law, or those which are known or suspected to be toxic to humans.

In accordance with another embodiment of the present invention there is described a nail enamel composition of non-toxic components for forming a film over natural or synthetic human nails, the composition comprising nitrocellulose having a molecular weight greater than 56,000, a solvent and aluminum platelets.

In accordance with another embodiment of the present invention there is described a method of forming a film containing aluminum platelets over natural or synthetic human nails, the method comprising coating a natural or synthetic human nail with an aqueous nail enamel composition to form a first film, and applying a nail enamel composition comprising a film forming component, a solvent and aluminum platelets over the first film to form a second film thereover, wherein the second film has a haze value when applied over the first film greater than a haze value when applied directly over said natural or synthetic human nails.

In accordance with another embodiment of the present invention there is described a nail enamel composition of non-toxic components for forming a film over natural or synthetic human nails, the composition comprising a film forming component, a solvent and aluminum platelets, wherein the solid content of the composition is in the range of from about 4 to about 20% by weight.

In accordance with another embodiment of the present invention there is described a nail enamel composition of non-toxic components for forming a film over natural or synthetic human nails, the composition comprising nitrocellulose having a molecular weight greater than 56,000, a solvent, a plasticizer, a suspending agent and aluminum platelets, the aluminum platelets having an aspect ratio of between about 1.0 to about 5.2 and a length in the range of about 3.6 microns to about 45.3 microns, the film having a haze value of about 975 HU and greater.

DETAILED DESCRIPTION OF THE PREFERRED EMBODIMENTS

In describing the preferred embodiments of the present invention, specific terminology will be resorted to for the sake of clarity. However, the invention is not intended to be limited to the specific terms so selected, and is to be understood that each specific term includes all technical equivalence which operate in a similar manner to accomplish a similar purpose.

Nail enamel compositions of the present invention for coating natural or synthetic human nails broadly include the ingredients of one or more film forming components, one or more solvents and aluminum particles in the form of platelets. The resulting composition will provide a nail enamel which forms a film upon drying having a mirrorlike appearance. In addition to the above components, the nail enamel compositions according to the present invention may further include one or more additional ingredients, for example, a thixotropic compound, a suspending agent, plasticizers, secondary pigments or colorants, one or more film forming resins, UV light absorbers, stabilizers, fragrances, moisturizers, leveling agents, drying agents and the like. In addition, if desired, the nail enamel compositions of the present invention may also include other pigments or organic coloring polymers to alter the film appearance as desired.

The nail enamel compositions of the present invention contain one or more primary film forming components such as polymers and the like. For example, suitable film forming compounds include cellulose acetate, cellulose acetate butyrate, ethyl cellulose, vinyl polymers, nitrocellulose, methacrylate and acrylate type polymers and co-polymers, and mixtures thereof. The preferred primary film forming compound for use in the present invention is nitrocellulose which provides an unusual combination of properties of toughness, durability, solubility and solvent release. Nitrocellulose is typically supplied in 70% concentrations, wet with 30% ethyl or isopropyl alcohol. As used in the present application, the percentage of nitrocellulose is given in a composition will be on a dry basis.

It has been discovered that film forming compounds having higher molecular weights will produce films having a mirrorlike appearance when incorporating aluminum platelets. In this regard, it was determined that as the molecular weight of the film forming compound increased, the mirrorlike appearance of the resulting nail enamel film improved as measured by its haze property as to be described hereinafter. By way of example, nitrocellulose as the film forming compound having an average molecular weight greater than 56,000 show improvements in mirror appearance. To this end, nitrocellulose as a film forming compound is available from a variety of sources, for example, Hercules, Inc. in various molecular weights. These grades of nitrocellulose include nitrocellulose RS½ sec. having a molecular weight of 56,000, nitrocellulose RS5–6 sec. having a molecular weight of 112,000, nitrocellulose RS15 sec. having a molecular weight of 130,000, nitrocellulose RS60–80 sec. having a molecular weight of 175,000, nitrocellulose RS150 sec. having a molecular weight of 190,000, as well as other grades having both lower and higher molecular weights.

Although nitrocellulose having higher molecular weights can also be used in the compositions of the present invention, they are less desirable due to their increased viscosity. It is contemplated that various grades of nitrocellulose can be used in combination as the film forming compounds of the present invention. For example, mixtures of low and high molecular weight nitrocellulose can be incorporated into the nail enamel compositions of the present invention to produce a film having a mirrorlike appearance. In particular, to improve the wear characteristics of the resulting film, the solid content of the nail enamel composition can be increased by using a mixture of lower grade nitrocellulose, e.g., RS¼ sec., and higher grade nitrocellulose, e.g., RS60–80 sec.

Other film forming compounds include cellulose acetate butyrate Product No. 381-20 having a molecular weight of about 83,000 which is available from Eastman. It is contemplated that other film forming compounds can be used having molecular weights sufficiently high to provide a nail enamel composition having enhanced mirror appearance. Nail enamel compositions of the present invention may include the above film forming compounds, their equivalence and combinations thereof in an amount ranging from about 2 to about 15% by weight, and more preferably in the range of about 4 to about 8% by weight of the composition.

In addition to the aforementioned film forming compounds, the nail enamel compositions can also include one or more modifying resins. Exemplary film resins which may be used in the present invention in combination with the film forming compounds include, for example, drying and non-drying alkyd resins, polyvinyl resins for example polyvinyl acetate, polyester resins, epoxy resins, acrylic polymers and copolymers, maleic modified glycerol esters of rosin, and toluene sulfonamide/epoxy resins, e.g., tosylamide epoxy resin. It is also within the scope of the present invention to include aldehyde condensation products such as arylsulfonamide formaldehyde resins, specifically toluene sulfonamide formaldehyde resin which is a condensation product of formaldehyde and toluene sulfonamide.

In addition to the film forming compounds, the nail enamel compositions according to the present invention may include at least one plasticizer to soften and plasticize particularly the film forming compounds. The plasticizer may be in either liquid or solid form, as well as combinations thereof. The compositions may include one or more of the known plasticizers which are suitable for use in nail enamel compositions. Examples of such known plasticizers include tricresyl phosphate, dibutyl tartrate, benzyl benzoate, tributyl phosphate, butyl acetyl ricinoleate, butyl glycolate, butyl stearate, sucrose acetate isobutyrate, triphenyl phosphate, triethyl citrate, camphor, castor oil, esters of citric, stearate, phalic, oleic, phosphate, butyric and benzoic acid, glyceryl triacetate and glyceryl triproprionate, 2,2,4-trimethyl-1,3-pentandiiol diisobutyrate and mixtures thereof. The nail enamel compositions of the present invention also contemplate the use of phthalate type plasticizers either alone or in combination with the aforementioned plasticizers, for example, diamylphthalate, dibutyl phthalate, diethyl phthalate, dioctyl phthalate, dibutoxy ethylphthalate and mixtures thereof. One preferred combination of plasticizers includes a mixture of dibutyl phthalate and sucrose acetate isobutyrate. Plasticizers included in the compositions of the present invention are in amounts sufficient to provide acceptable flexibility to the nail enamel film on the human or synthetic nail surface.

The nail enamel compositions of the present invention also include one or more organic solvents such as those generally used in conventional nail enamel compositions. Examples of these solvents include ethyl acetate, methyl acetate, ethanol, isopropanol, propyl acetate, n-butanol, xylene, DI acetone alcohol, aromatic (containing phenyl groups), amyl acetate, ethers, ketones, alkanes for example, pentane, cyclopentane, hexane, toluene, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, chlorinated hydrocarbons for example, methylene chloride, chloroform and methylchloroform. The aforementioned solvents can be used alone or in mixtures thereof. In general, the amount of solvent used in the compositions of the present invention range from about 80 to about 96% by weight, and preferably about 85 to about 90% by weight of the composition.

The mirrorlike appearance of the nail enamel composition is provided by the presence of aluminum platelets sold under the mark Metalure®. The Metalure® aluminum platelets have a minimum aspect ratio of 1.0 and a maximum aspect ratio of about 5.2, the mean being about 1.507. The aspect ratio of the aluminum platelets is defined as the ratio of the major dimension (length) to the minor dimension (width). The Metalure® aluminum platelets have a particle size distribution as follows:

| PARTICLE SIZE DISTRIBUTION (Length/Microns) | | |
|---|---|---|
| Low | High | Cumulative % |
| 3.600 | 4.900 | 15.330 |
| 4.908 | 7.950 | 33.800 |
| 7.957 | 10.630 | 48.200 |
| 10.663 | 14.208 | 62.410 |
| 14.209 | 18.980 | 81.170 |
| 18.986 | 27.940 | 94.320 |
| 27.945 | 37.340 | 96.790 |
| 37.342 | 45.300 | 100.000 |

It has been reported that these aluminum platelets will not destabilize under high sheer. However, excessive mixing can potentially cause mechanical breakage and attrition of the optimized particle size distribution, resulting in reduced brilliance. To this end, it is contemplated that mixing in mechanical mills such as ball or sand mills would not be desirable in making nail enamel compositions in accordance with the present invention. The nail enamel compositions of the present invention may include aluminum platelets in an amount ranging from about 0.1 to about 5% by weight, and preferably in the range of about 0.3 to about 1.5% by weight of the composition.

Additionally, secondary pigments and/or organic colorants can be added to the compositions to provide cosmetically acceptable shades and to pacify the films. Pigments and/or organic colorants for use in the present invention may include any of those pigments or organic colorants which are generally known for use in nail enamel compositions. For example, pigments can include cosmetic grade or purified titanium dioxide, yellow and red iron oxides, bismuth oxychloride, iron blue, iron black, mica particles, ultramarine blue, D&C Red #7, chromide oxide greens, carbon black, lampblack and the like. Other pigments which may be used in compositions according to the present invention may include the Lake pigments, for example, D&C Red #6 barium Lake, D&C Red #7 calcium Lake and the like.

In addition to the above named pigments, there may also be included titanated micas, polyethylene teraphthalates and pearl essence which is a suspension of crystalline guanine in nitrocellulose and solvents, as well as other additives which will affect the appearance of the pigment. The amount of pigment in the compositions of the present invention will vary as a function of the type of pigment and other components included in the composition.

It is useful to include a suspending agent for enhancing the suspension of the aluminum platelets or other pigments in the other components of the nail enamel composition. A number of suspending agents, either alone or in combination, which are generally used in conventional nail enamel compositions may be used to produce compositions according to the present invention. For example, suspending agents include colloidal clays, montmorillonite clays, especially stearalkonium hectorite, stearalkonium bentonite, fumed silica, and mixtures thereof. One preferred combination of suspending agents include bentonite and a modified lower molecular weight polymeric urea available from BYK-Chemie USA, Wallingford, Connecticut sold under the name BYK-410. The suspending agent is present in the compositions of the present invention in amounts sufficient to produce a gel, preferably a colloidal gel. It is also contemplated that the polymeric urea can be used alone as a suspending agent.

In addition to the above described components, the nail enamel compositions of the present invention may also include additional additives including stabilizers, thixotropic agents, UV light absorbers such as ectocrylene and benzophenone-1, fragrances, moisturizers and medicants, depending on the intended result. These components are well known in the art and may be included in amounts well within the teachings of the prior art.

The incorporation of higher molecular weight components into the nail enamel composition of the present invention has the tendency to increase the composition viscosity. To maintain the composition in a flowable state to allow smooth and even application to one's nails, the percentage of solids in the composition can be reduced. By way of example, the solid content of the nail enamel compositions of the present invention ranges from about 4 to about 20% by weight, and preferably from about 10 to about 15% by weight.

The nail enamel compositions in accordance with the present invention can be manufactured by thoroughly and intimately mixing together all the components in the amounts described in accordance with the present invention. Examples of satisfactory equipment and how to use then are readily apparent to one of ordinary skill in the nail enamel art.

In order to evaluate the mirror appearance of various nail enamel compositions prepared which include aluminum platelets, an instrument known as a goniophotometer was used. A goniophotometer is an instrument for measuring the angular distribution of reflected or transmitted light. In this regard, the mirrorlike appearance of nail enamel compositions which include aluminum platelets can be described by its gloss characteristics. The term "gloss" is defined in ASTM standard E284(3) entitled Terminology of Appearance as angular selectivity of reflectance, involving surface-reflected light, responsible for the degree to which reflected highlights or images of objects may be seen as superimposed on a surface. Angular selectivity falls into various types such as specular gloss, sheen and haze. "Specular gloss" is defined in the aforementioned ASTM standard as the ratio of flux reflected in specular direction to incident flux for a specified angle of incidence and source and receptor angle apertures. "Sheen" is defined in the aforementioned ASTM standard as the specular gloss at a large angle of incidence for an otherwise matte specimen. Haze in coating films is often designated "reflection haze" because in plastics there is encountered a near-forward scattering in transmission that is designated transmission haze. The aforementioned ASTM standard defines "haze" in reflection as percent of reflected light scattered by a specimen having a glossy surface so that its direction deviates more than a specified angle from the direction of specular reflection.

One instrument suitable for measuring the properties of haze and gloss of a film is available from BYK Gardner USA of Columbia, Md., Catalog No. LGB-4601. The haze-gloss instrument is constructed in accordance with ASTM standard E430-97 entitled Method for Measurement of Gloss of High Gloss Surfaces by Goniophotometry.

The following examples illustrate nail enamel compositions incorporating aluminum platelets. These examples are by way of illustration and are not intended to be limiting of the present invention either as to the inclusion of a greater or lesser number of components, the substitution of additional components or variations in the percentages of the range of components. In order to evaluate the mirrorlike appearance of the resulting films formed from these compositions, the aforementioned haze-gloss instrument was utilized to determine haze. The haze-gloss instrument measures haze in the range of from 10–2,500 HU, i.e., haze units (Hlog). Samples for evaluation were prepared in accordance with ASTM standard G147-July 96 entitled Standard Practice for Conditioning and Handling of Non-Metallic Materials for Natural and Artificial Weathering Tests. The samples were based upon a dried 3 mil wet film drawn on a substrate obtained from The Linetta Company of Mahwah, N.J.

EXAMPLE 1
(HAZE = 1097 HU)

| | Wt. % |
|---|---|
| METALURE L 55350 | 0.75 |
| BUTYL ACETATE | 28.79 |
| ETHYL ACETATE | 57.80 |
| ISOPROPYL ALCOHOL | 3.84 |
| DIMETHICONE | 0.01 |
| CELLULOSE ACETATE BUTYRATE 381-20 (MW-83,000) | 6.31 |
| DIBUTYL PHTHALATE | 1.69 |
| CAMPHOR | 0.81 |

EXAMPLE 2
(HAZE = 460 HU)

| | Wt. % |
|---|---|
| METALURE L 55350 | 0.75 |
| BUTYL ACETATE | 28.80 |
| ETHYL ACETATE | 57.74 |
| ISOPROPYL ALCOHOL | 3.90 |
| DIMETHICONE | 0.01 |
| ACRYLOID B66 (MW-60,000) | 6.31 |
| DIBUTYL PHTHALATE | 1.70 |
| CAMPHOR | 0.80 |

EXAMPLE 3
(HAZE = 932 HU)

| | Wt. % |
|---|---|
| METALURE L 55350 | 0.75 |
| BUTYL ACETATE | 28.79 |
| ETHYL ACETATE | 54.76 |
| ISOPROPYL ALCOHOL | 5.79 |
| DIMETHICONE | 0.01 |
| NITROCELLULOSE ½ sec. (MW-56,000) | 4.41 |
| DIBUTYL PHTHALATE | 1.69 |
| CAMPHOR | 0.80 |

EXAMPLE 4
(HAZE = 1323 HU)

| | Wt. % |
|---|---|
| METALURE L 55350 | 0.40 |
| BUTYL ACETATE | 32.19 |
| ETHYL ACETATE | 54.89 |
| ISOPROPYL ALCOHOL | 1.86 |
| ETHYL ALCOHOL | 5.50 |
| DIMETHICONE | 0.01 |
| NITROCELLULOSE 15–35 sec. (MW-130,000) | 4.35 |
| CAMPHOR | 0.80 |

EXAMPLE 5
(HAZE = 1365 HU)

| | Wt. % |
|---|---|
| METALURE L 55350 | 0.40 |
| BUTYL ACETATE | 32.19 |
| ETHYL ACETATE | 54.89 |
| ISOPROPYL ALCOHOL | 1.86 |
| ETHYL ALCOHOL | 5.50 |
| DIMETHICONE | 0.01 |
| NITROCELLULOSE 150 sec. (MW-190,000) | 4.35 |
| CAMPHOR | 0.80 |

EXAMPLE 6
(HAZE = 1342 HU)

| | Wt. % |
|---|---|
| METALURE L 55350 | 0.40 |
| BUTYL ACETATE | 32.19 |
| ETHYL ACETATE | 54.89 |
| ISOPROPYL ALCOHOL | 1.86 |
| ETHYL ALCOHOL | 5.50 |
| DIMETHICONE | 0.01 |
| NITROCELLULOSE 60–80 sec. (MW-175,000) | 4.35 |
| CAMPHOR | 0.80 |

EXAMPLE 7
(HAZE = 1240 HU)

| | Wt. % |
|---|---|
| METALURE L 55350 | 0.75 |
| BUTYL ACETATE | 28.79 |
| ETHYL ACETATE | 57.80 |
| ISOPROPYL ALCOHOL | 5.74 |
| ETHYL ALCOHOL | 5.50 |
| DIMETHICONE | 0.01 |
| NITROCELLULOSE 60–80 sec. | 4.41 |
| DIBUTYL PHTHALATE | 1.69 |
| CAMPHOR | 0.80 |

EXAMPLE 8
(HAZE = 986 HU)

| | Wt. % |
|---|---|
| METALURE L 55350 | 0.75 |
| BUTYL ACETATE | 32.08 |
| ETHYL ACETATE | 54.41 |
| ISOPROPYL ALCOHOL | 4.04 |
| POLYESTER RESIN | 1.75 |
| DIMETHICONE | 0.01 |
| NITROCELLULOSE 5–6 sec. (MW-112,000) | 4.41 |
| DIBUTYL PHTHALATE | 1.75 |
| CAMPHOR | 0.80 |

EXAMPLE 9
(HAZE = 1180 HU)

| | Wt. % |
|---|---|
| METALURE L 55350 | 0.50 |
| BUTYL ACETATE | 22.87 |
| ETHYL ACETATE | 57.60 |
| SD ALCOHOL 40B | 6.10 |
| ISOPROPYL ALCOHOL | 5.74 |
| NITROCELLULOSE 60–80 sec. | 4.30 |
| ISOPROPYL ALCOHOL | 4.47 |
| CAMPHOR | 0.80 |
| SUCROSE ACETATE ISOBUTYRATE | 1.30 |
| STEARALKONIUM HECTORITE | 1.05 |
| DIMETHICONE | 0.01 |
| DIBUTYL PHTHALATE | 0.80 |
| BYK410 | 0.20 |

EXAMPLE 10
(HAZE = 850 HU)

| | Wt. % |
|---|---|
| METALURE L 55350 | 0.75 |
| BUTYL ACETATE | 28.79 |
| ETHYL ACETATE | 57.80 |
| ISOPROPYL ALCOHOL | 3.84 |
| DIMETHICONE | 0.01 |
| CELLULOSE ACETATE BUTYRATE | 6.31 |
| DIBUTYL PHTHALATE | 1.69 |
| CAMPHOR | 0.81 |

EXAMPLE 11
(HAZE = 1126 HU)

| | Wt. % |
|---|---|
| METALURE L 55350 | 0.50 |
| BUTYL ACETATE | 24.00 |
| ETHYL ACETATE | 40.64 |
| ETHYL ALCOHOL | 9.00 |
| NITROCELLULOSE 60–80 sec. | 3.90 |
| NITROCELLULOSE ¼ sec. | 3.40 |
| ISOPROPYL ALCOHOL | 6.30 |
| CAMPHOR | 1.35 |
| SUCROSE ACETATE ISOBUTYRATE | 2.30 |
| DIMETHICONE | 0.01 |
| BYK410 | .20 |
| AMYL ACETATE | 5.00 |

-continued

EXAMPLE 11
(HAZE = 1126 HU)

| | Wt. % |
|---|---|
| DIBUTYL PHTHALATE | 1.60 |
| DIACETONE ALCOHOL | .70 |
| STEARALKONIUM HECTORITE | 1.10 |

EXAMPLE 12
(HAZE = 978 HU)

| | Wt. % |
|---|---|
| METALURE L 55350 | 0.50 |
| BUTYL ACETATE | 24.00 |
| ETHYL ACETATE | 40.15 |
| ETHYL ALCOHOL | 9.00 |
| NITROCELLULOSE 60–80 sec. | 3.85 |
| NITROCELLULOSE ¼ sec. | 3.40 |
| ISOPROPYL ALCOHOL | 6.30 |
| CAMPHOR | 1.35 |
| POLYESTER RESIN | 0.30 |
| SUCROSE ACETATE ISOBUTYRATE | 2.30 |
| DIMETHICONE | 0.01 |
| BYK410 | 0.20 |
| AMYL ACETATE | 4.90 |
| DIBUTYL PHTHALATE | 1.58 |
| DIACETONE ALCOHOL | 0.70 |
| STEARALKONIUM HECTORITE | 1.10 |
| D&C RED #6 BARIUM LAKE | 0.36 |

EXAMPLE 13
(HAZE = 857 HU)

| | Wt. % |
|---|---|
| METALURE L 55350 | 0.30 |
| BUTYL ACETATE | 24.00 |
| ETHYL ACETATE | 39.88 |
| ETHYL ALCOHOL | 9.00 |
| NITROCELLULOSE 60–80 sec. | 3.80 |
| NITROCELLULOSE ¼ sec. | 3.40 |
| ISOPROPYL ALCOHOL | 6.30 |
| CAMPHOR | 1.35 |
| POLYESTER RESIN | 0.60 |
| SUCROSE ACETATE ISOBUTYRATE | 2.20 |
| DIMETHICONE | 0.01 |
| BYK410 | 0.20 |
| AMYL ACETATE | 4.90 |
| DIBUTYL PHTHALATE | 1.55 |
| DIACETONE ALCOHOL | 0.68 |
| STEARALKONIUM HECTORITE | 1.10 |
| D&C RED #6 BARIUM LAKE | 0.73 |

In considering the foregoing examples, nail enamel compositions having a measured haze in the order of 930 HU evidence minimal mirror appearance in the resulting films. That is, the resulting film although possessing an aluminum color lacks the ability to reflect distinguishing features of an object. These examples evidence that the mirrorlike appearance, as measured by haze values, is improved as the molecular weight of the resulting film increases. By way of example, increased molecular weight of the overall film is a function of not only the primary film forming compound, but also any modifying resin and the incorporation of plasticizers and the like. In the case of nitrocellulose as the primary film forming compound, improvements in mirror appearance were obtained as the molecular weight of the nitrocellulose increased above 56,000. In this regard, significant improvement in the mirror appearance was achieved using nitrocellulose having a molecular weight of 112,000 producing a film having a measured haze of 986 HU. In a similar manner, increasing the molecular weight of cellulose acetate butyrate as the primary film former from 30,000 to 83,000 increased the mirror appearance as measured by haze from 850 HU to 1,097 HU. The addition of lower molecular weight components, e.g., dibutyl phthalate and polyester resin affected the mirror appearance as evidenced by the lower haze measurements, i.e., 1,342 vs. 1,240.

In accordance with the present invention, nail enamel compositions which include aluminum platelets can produce a mirrorlike appearance having a measured haze greater than 932 HU, and preferably greater than 975 HU, which haze values are based on films without secondary pigments of the type noted hereinabove. The films can achieve these values and mirrorlike appearance by selecting the film forming polymer and resulting composition to have a sufficiently high molecular weight. Once the particular type of film forming compound is selected, e.g., nitrocellulose, cellulose acetate butyrate, etc., compounds of varying molecular weight can be evaluated for the resulting mirror appearance as measured by haze. These results will be influenced by the molecular weight of the other components which are added to the nail enamel composition, for example, plasticizers, resins and the like. From the foregoing, one can produce a nail enamel composition in accordance with the present invention having a mirrorlike appearance based upon selected components, e.g., film formers, plasticizers, etc.

The nail enamel compositions of the present invention are generally applied directly over one's nail. However, these compositions may be applied over base coats which are clear or are pigmented. It has been discovered that by applying the nail enamel compositions of the present invention over a base coat which is formulated as an aqueous emulsion or dispersion enhanced mirrorlike appearance is achieved. Suitable base coat aqueous dispersions and emulsions are known from U.S. patent application Ser. No. 09/327,799 filed on Jun. 8, 1999 entitled NAIL ENAMEL COMPOSITIONS HAVING DECORATIVE APPEARANCE, the disclosure of which is incorporated herein by reference, and which application is assigned to the assignee of the present application. Accordingly, it is contemplated that nail enamel compositions based upon lower molecular weight film forming compounds can have enhanced mirrorlike appearance when applied over base coats based upon aqueous dispersions or emulsions.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A nail enamel composition of non-toxic components for forming a film over natural or synthetic human nails, said composition comprising a film forming component, a solvent and aluminum platelets, said film having a haze value greater than 932 HU.

2. The composition of claim 1, wherein said film forming component comprises nitrocellulose.

3. The composition of claim 2, wherein said nitrocellulose has a molecular weight greater than 56,000.

4. The composition of claim 2, wherein said nitrocellulose has a molecular weight greater than about 112,000.

5. The composition of claim 1, wherein said film forming component comprises cellulose acetate butyrate.

6. The composition of claim 5, wherein said cellulose acetate butyrate has a molecular, weight of about 83,000 and greater.

7. The composition of claim 1, wherein said aluminum platelets are suspended in an organic solvent.

8. The composition of claim 1, wherein said organic solvent is selected from the group consisting of toluene, normal propyl acetate, isopropyl acetate, isopropyl alcohol, ethyl acetate, glycol ether pm, normal butyl acetate, methyl proposol acetate and mixtures thereof.

9. The composition of claim 1, further comprising a plasticizer and a suspading agent.

10. The composition of claim 1, wherein said aluminum platelets have an aspect ratio of between about 1.0 to about 5.2.

11. The composition of claim 1, wherein said aluminum platelets have a mean aspect ratio of about 1.507.

12. The composition of claim 1, wherein said aluminum particles have a length in the range of from about 3.6 microns to about 45.3 microns.

13. The composition of claim 12, wherein said aluminum platelets have an aspect ratio of between about 1.0 to about 5.2.

14. The composition of claim 12, wherein said aluminum platelets have a mean aspect ratio of about 1.507.

15. The composition of claim 1, wherein said haze value is greater than about 975 HU.

16. The composition of claim 1, wherein said aluminum platelets are present in the range of from about 0.1 to about 5% by weight of said composition.

17. The composition of claim 1, wherein the solid content of said composition is in the range of from about 10 to about 15% by weight of said composition.

18. A nail enamel composition of non-toxic components for forming a film over natural or synthetic human nails, said composition comprising nitrocellulose having a molecular weight greater than 56,000, a solvent and aluminum platelets.

19. The composition of claim 18, wherein said nitrocellulose has a molecular weight greater than about 112,000.

20. The composition of claim 18, wherein said aluminum platelets are suspended in an organic solvent.

21. The composition of claim 20, wherein said organic solvent is selected from the group consisting of toluene, normal propyl acetate, isopropyl acetate, isopropyl alcohol, ethyl acetate, glycol ether pm, normal butyl acetate, methyl proposol acetate and mixtures thereof.

22. The composition of claim 18, further comprising a plasticizer and a suspending agent.

23. The composition of claim 22, wherein said plasticizer comprises a mixture of dibutyl phthalate and sucrose acetate isobutyrate.

24. The composition of claim 23, wherein said suspending agent comprises a mixture of bentonite and polymeric urea.

25. The composition of claim 18, wherein said aluminum platelets have an aspect ratio of between about 1.0 to about 5.2.

26. The composition of claim 18, wherein said aluminum platelets have a mean aspect ratio of about 1.507.

27. The composition of claim 18, wherein said aluminum particles have a length in the range of from about 3.6 microns to about 45.3 microns.

28. The composition of claim 27, wherein said aluminum platelets have an aspect ratio of between about 1.0 to about 5.2.

29. The composition of claim 27, wherein said aluminum platelets have a mean aspect ratio of about 1.507.

30. The composition of claim 18, wherein said aluminum platelets are present in the range of from about 0.1 to about 5% by weight of said composition.

31. The composition of claim 18, wherein said aluminum platelets have a mean aspect ratio of about 1.507.

32. The composition of claim 18, wherein the solid content of said composition is in the range of from about 10 to about 15% by weight of said composition.

33. The composition of claim 18, wherein said film has a haze value greater than about 975 HU.

34. A method of forming a film containing aluminum platelets over natural or synthetic human nails, said method comprising coating a natural or synthetic human nail with an aqueous nail enamel composition to form a first film, and applying a nail enamel composition comprising a film forming component, a solvent and aluminum platelets over said first film to form a second film thereover, wherein said second film has a haze value when applied over said first film greater than a haze value when applied directly over said natural or synthetic human nails.

35. The method of claim 34, wherein said aqueous nail enamel composition includes a film forming component and water.

36. The method of claim 34, wherein said film forming component comprises nitrocellulose.

37. The method of claim 36, wherein said nitrocellulose has a molecular weight greater than 56,000.

38. The method of claim 36, wherein said nitrocellulose has a molecular weight greater than about 112,000.

39. The method of claim 34, wherein said film forming component comprises cellulose acetate butyrate.

40. The method of claim 39, wherein said cellulose acetate butyrate has a molecular weight of about 83,000 and greater.

41. The method of claim 34, wherein said aluminum platelets are suspended in an organic solvent.

42. The method of claim 41, wherein said organic solvent is selected from the group consisting of toluene, normal propyl acetate, isopropyl acetate, isopropyl alcohol, ethyl acetate, glycol ether pm, normal butyl acetate, methyl proposol acetate and mixtures thereof.

43. The method of claim 34, further including a plasticizer and a suspending agent.

44. The method of claim 34, wherein said aluminum platelets have an aspect ratio of between about 1.0 to about 5.2.

45. The method of claim 34, wherein said aluminum platelets have a mean aspect ratio of about 1.507.

46. The method of claim 34, wherein said aluminum particles have a length in the range of from about 3.6 microns to about 45.3 microns.

47. The method of claim 46, wherein said aluminum platelets have an aspect ratio of between about, 1.0 to about 5.2.

48. The method of claim 46, wherein said aluminum platelets have a mean aspect ratio of about 1.507.

49. A nail enamel composition of non-toxic components for forming a film over natural or synthetic human nails, said composition comprising a film forming component, a solvent and aluminum platelets, wherein the solid content of said composition is in the range of from about 4 to about 20% by weight.

50. The composition of claim 49, wherein said film has a haze value of about 975 HU and greater.

51. The composition of claim 49, further comprising a plasticizer and a suspending agent.

52. The composition of claim 49, wherein said aluminum platelets have an aspect ratio of between about 1.0 to about 5.2.

53. The composition of claim 49, wherein said aluminum platelets have a mean aspect ratio of about 1.507.

54. The composition of claim 49, wherein said aluminum particles have a length in the range of from about 3.6 microns to about 45.3 microns.

55. The composition of claim 54, wherein said aluminum platelets have an aspect ratio of between about 1.0 to about 5.2.

56. The composition of claim 54, wherein said aluminum platelets have a mean aspect ratio of about 1.507.

57. The composition of claim 49, wherein said film forming component comprises nitrocellulose.

58. The composition of claim 57, wherein said nitrocellulose has a molecular weight greater than about 112,000.

59. The composition of claim 49, wherein said aluminum platelets are present in the range of from about 0.1 to about 5% by weight of said composition.

60. The composition of claim 49, wherein the solid content of said composition is in the range of from about 10 to about 15% by weight of said composition.

61. The composition of claim 49, wherein said film has a haze value greater than about 932 HU.

62. A nail enamel composition of non-toxic components for forming a film over natural or synthetic human nails, said composition comprising nitrocellulose having a molecular weight greater than 56,000, a solvent, a plasticizer, a suspending agent and aluminum platelets, said aluminum platelets having an aspect ratio of between about 1.0 to about 5.2 and a length in the range of about 3.6 microns to about 45.3 microns, said film having a haze greater than 932 HU.

63. The composition of claim 62, wherein the solid content of said composition is in the range of from about 4 to about 20% by weight of said composition.

64. The composition of claim 62, further comprising nitrocellulose having a molecular weight less than 56,000.

65. The composition of claim 62, wherein said aluminum platelets are present in the range of from about 0.1 to about 5% by weight of said composition.

66. The composition of claim 62, wherein said haze value is greater than about 975 HU.

67. The composition of claim 62, wherein the solid content of said composition is in the range of from about 10 to about 15% by weight of said composition.

68. A method of forming a film over natural or synthetic human nails, said method comprising providing a nail enamel composition as set forth in claim 62, and applying said composition over said nails.

69. A method of forming a film over natural or synthetic human nails, said method comprising providing a nail enamel composition as set forth in claim 1, and applying said composition over said nails.

70. A method of forming a film over natural or synthetic human nails, said method comprising providing a nail enamel composition as set forth in claim 18 and applying said composition over said nails.

71. A method of forming a film over natural or synthetic human nails, said method comprising providing a nail enamel composition as set forth in claim 49, and applying said composition over said nails.

72. The nail enamel composition of claim 49, which has a mirror appearance.

73. The composition of claim 1, wherein said aluminum platelets consist essentially of aluminum.

74. The composition of claim 18, wherein said aluminum platelets consists essentially of aluminum.

75. The method of claim 34, wherein said aluminum platelet consists essentially of aluminum.

76. The composition of claim 49, wherein said aluminum platelet consist essentially of aluminum.

77. The composition of claim 62, wherein said aluminum platelets consist essentially of aluminum.

78. The method of claim 68, wherein said aluminum platelets consist essentially of aluminum.

79. The method of claim 69, wherein said aluminum platelets consist essentially of aluminum.

80. The method of claim 70, wherein said aluminum platelets consist essentially of aluminum.

81. The method of claim 71, wherein said aluminum platelets consists essentially of aluminum.

* * * * *

UNITED STATES PATENT AND TRADEMARK OFFICE
CERTIFICATE OF CORRECTION

PATENT NO. : 6,565,835 B1
DATED : May 20, 2003
INVENTOR(S) : Robert L. Socci and Anatoly Ismailer It is certified that error appears in the above-identified patent and that said Letters Patent is hereby corrected as shown below:

<u>Title page,</u>
Item [73], Assignee, "Patterson" should read -- Paterson --.

<u>Column 13,</u>
Line 15, "suspading" should read -- suspending --.

<u>Column 16,</u>
Lines 26 and 41, "consists" should read -- consist --.
Line 30, "consist" should read -- consists --.

Signed and Sealed this

Ninth Day of September, 2003

JAMES E. ROGAN
*Director of the United States Patent and Trademark Office*